Figure 1:
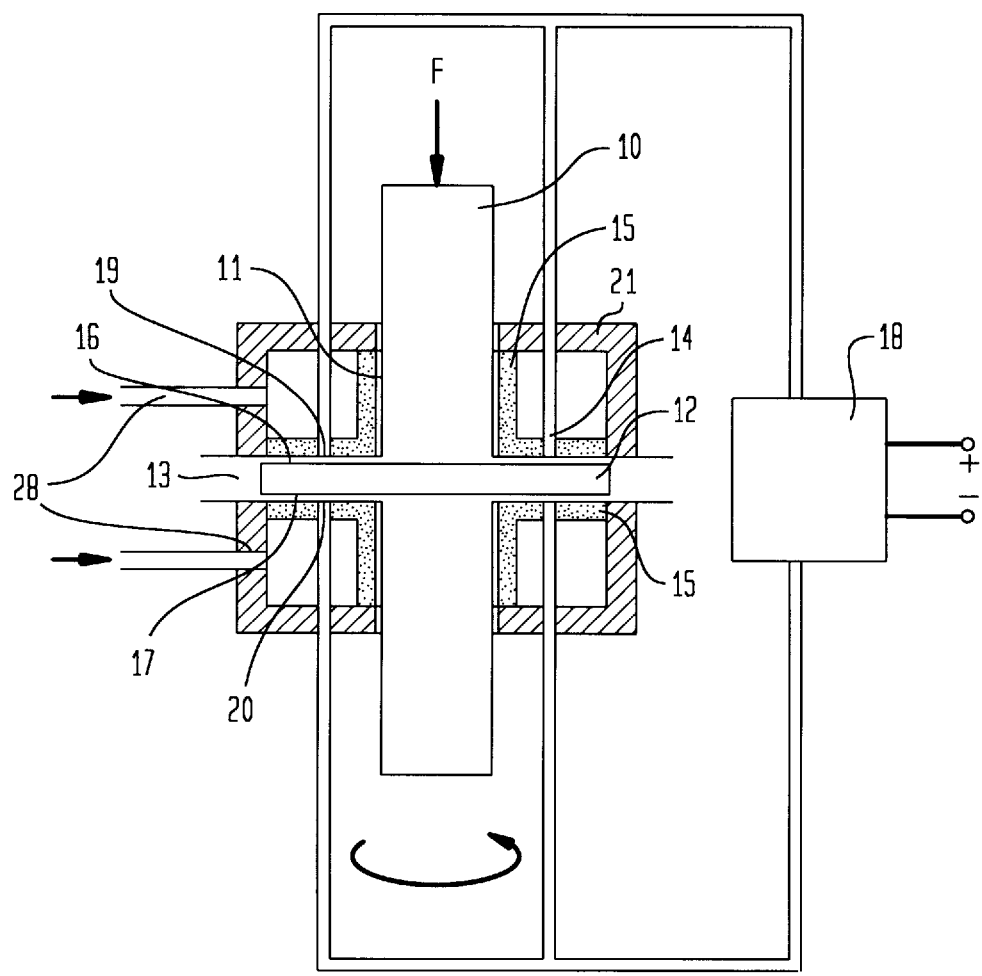

United States Patent [19]
Larsson

[11] Patent Number: 5,886,268
[45] Date of Patent: Mar. 23, 1999

[54] PRESSURE MEASURING DEVICE

[75] Inventor: Sven-Erik Larsson, Åkarp, Sweden

[73] Assignee: Reologica Instruments AB, Lund, Sweden

[21] Appl. No.: 930,807

[22] PCT Filed: Apr. 11, 1996

[86] PCT No.: PCT/SE96/00473

§ 371 Date: Oct. 8, 1997

§ 102(e) Date: Oct. 8, 1997

[87] PCT Pub. No.: WO96/32630

PCT Pub. Date: Oct. 17, 1996

[30] Foreign Application Priority Data

Apr. 11, 1995 [SE] Sweden ................................... 9501334

[51] Int. Cl.[6] .................................................. G01L 1/02
[52] U.S. Cl. .............................. 73/862.583; 73/862.581; 73/862.49
[58] Field of Search ........................ 73/862.581–862.584, 73/862.49

[56] References Cited

U.S. PATENT DOCUMENTS

| | | | |
|---|---|---|---|
| 1,298,630 | 3/1919 | Schmidt | 73/862.582 |
| 2,517,038 | 8/1950 | Sheffield | 73/140 |
| 2,885,889 | 5/1959 | Trimmer | 73/862.583 |
| 2,908,164 | 10/1959 | Bamber | 73/862.583 |
| 3,411,349 | 11/1968 | Smith et al. | 73/862.582 |
| 3,828,610 | 8/1974 | Swearingen | 73/140 |
| 4,040,300 | 8/1977 | Negard | 73/459 |
| 4,222,491 | 9/1980 | Geppert | 212/153 |
| 4,287,758 | 9/1981 | Swearingen | 73/862.49 |

FOREIGN PATENT DOCUMENTS

| | | |
|---|---|---|
| 21 58 607 | 7/1972 | Germany . |
| 2 173 599 | 8/1986 | United Kingdom . |

*Primary Examiner*—Ronald Biegel
*Attorney, Agent, or Firm*—Mathews, Collins, Sheperd & Gould, P.A.

[57] ABSTRACT

A method for measurement of axial forces acting on a shaft, being supplied with gas under overpressure such that gas pressure is built up between two opposing faces of said portion projecting radially from the shaft and at least one gas-permeable body provided external to said faces. A gas differential between the gas pressure on said opposing faces is established, and the axial force acting on said shaft is determined as a product of a constant and the pressure differential between the gas pressures on the two faces. Means are provided for supply of gas under overpressure to said body and pressure measuring means are provided for measurement of the pressure differential between the pressures on the two faces of the radially projecting portion. The protruding portion may also constitute a measuring plate which, provided in various manners, is subjected to forces.

19 Claims, 7 Drawing Sheets

PRESSURE MEASURING DEVICE

TECHNICAL BACKGROUND

The invention is related to a method and a device for measurement of axial forces acting on an shaft. The invention also involves a method and a device for measuring the force on a measuring plate.

When taking measurements with certain types of measuring assemblies the need arises to measure axial forces which work on a rotating shaft or similar machine element. The axial force can be an integral part of the properties to be measured, but it may also be that the measurement of the axial force is a factor or condition connected with measurement of other forces or properties.

Force measurement is also used generally for measurement of, for example, forces which act against a measuring plate and which correspond to torque on an shaft.

STATE OF THE ART

Since the shaft is rotating during measurement, or can be rotated, certain problems occur partly in connection with recording the measurement signal and partly with transmitting the measurement signal to non-rotating parts of the measuring assembly. One customary method of avoiding these problems is to measure an axial displacement or motion caused by the force on the element by means of an indirect method instead of measuring the actual force which affects an shaft or another rotating element.

Use of such techniques brings about other problems instead, for example lessened exactness of measurement, decreased repeatability, and increased risk that the recorded measurement signals may wander.

Other problems which generally occur with devices for measurement of forces and torques are drift of the measurement signal as a result of high amplification and similar.

THE INVENTION IN SUMMARY

One objective of the present invention is to eliminate the above problems using indirect methods of measurement. The objective is achieved by means of the special features adapted by the invention, as indicated by patent claims 1 and 2. With these special features the invention has also been provided with other improved characteristics, which can be seen from the description below and the following patent claims. In an especially preferred embodiment a so-called air bearing, which is already well-known, has been modified and further developed. The method and device according to the invention are especially suitable for use within rheology, i.e., the measurement of the viscoelastic properties of a substance.

Another objective is to achieve a measuring device with low or undetectable drift and one which exhibits self-stabilizing characteristics. With the invention it also becomes possible to place required electronic components at a distance from the actual place of measurement.

The above indicated objectives are achieved by the invention's incorporation of the characteristics indicated in the independent patent claims given below. Further objectives and advantages with the invention emerge from the following description, drawings, and dependent patent claims.

SHORT DESCRIPTION OF THE DRAWINGS

Figure 2:
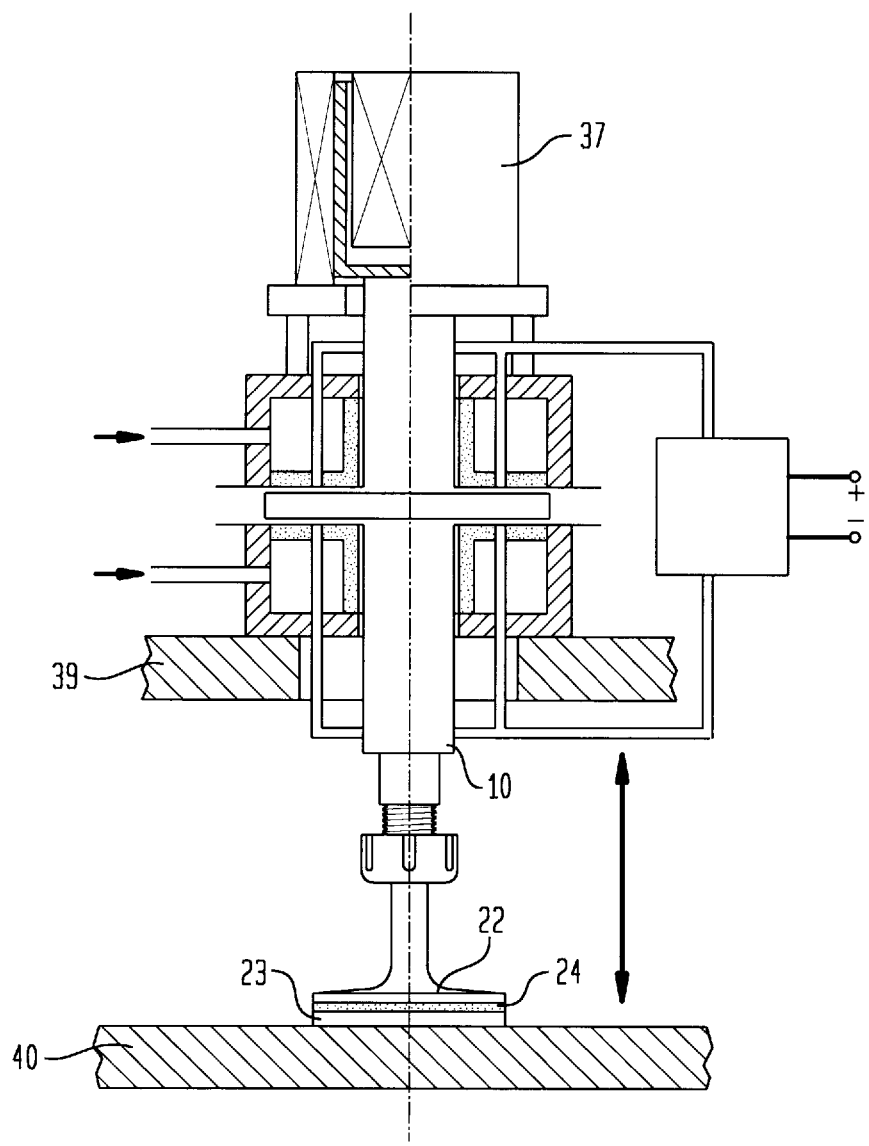
Figure 3:
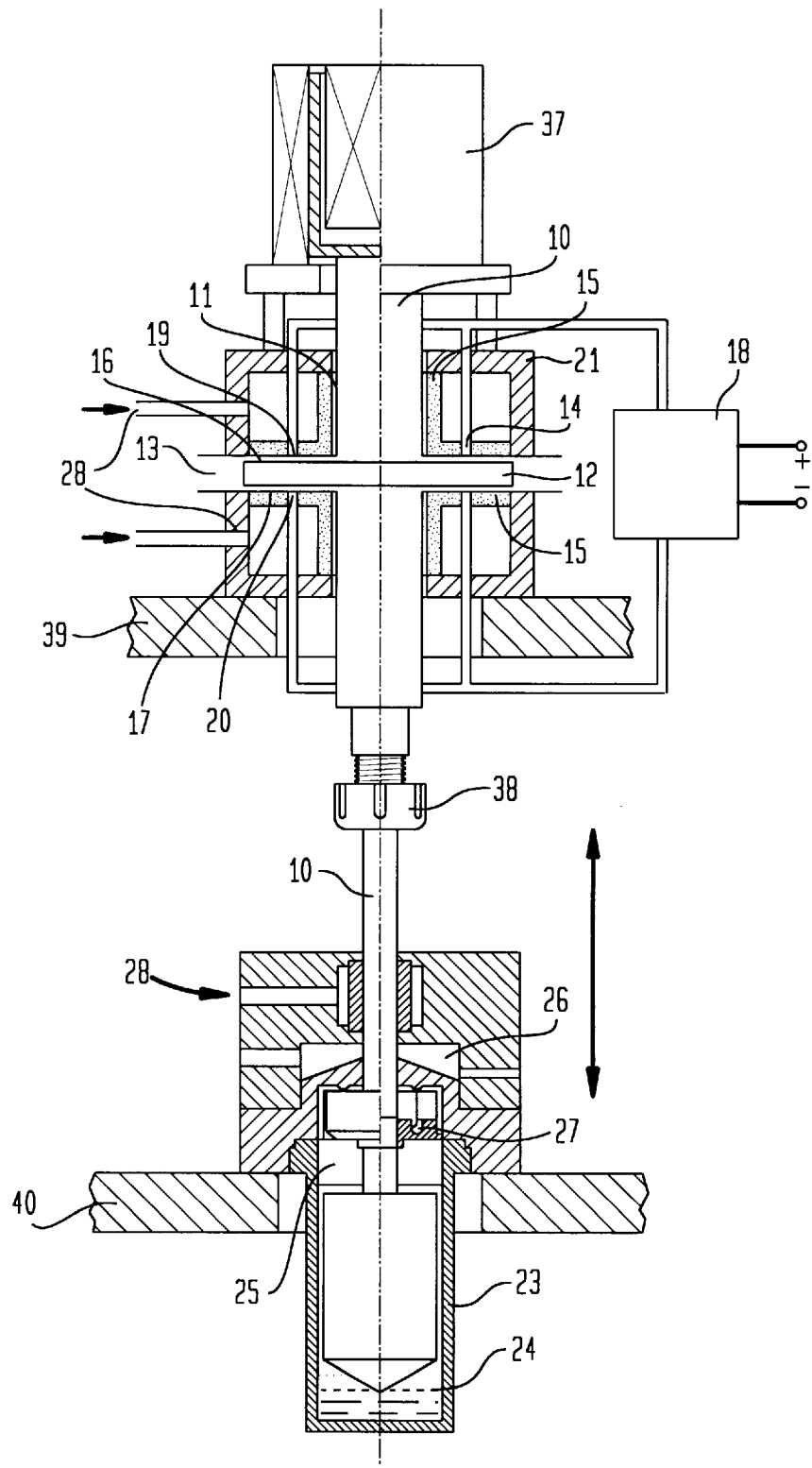
Figure 4:
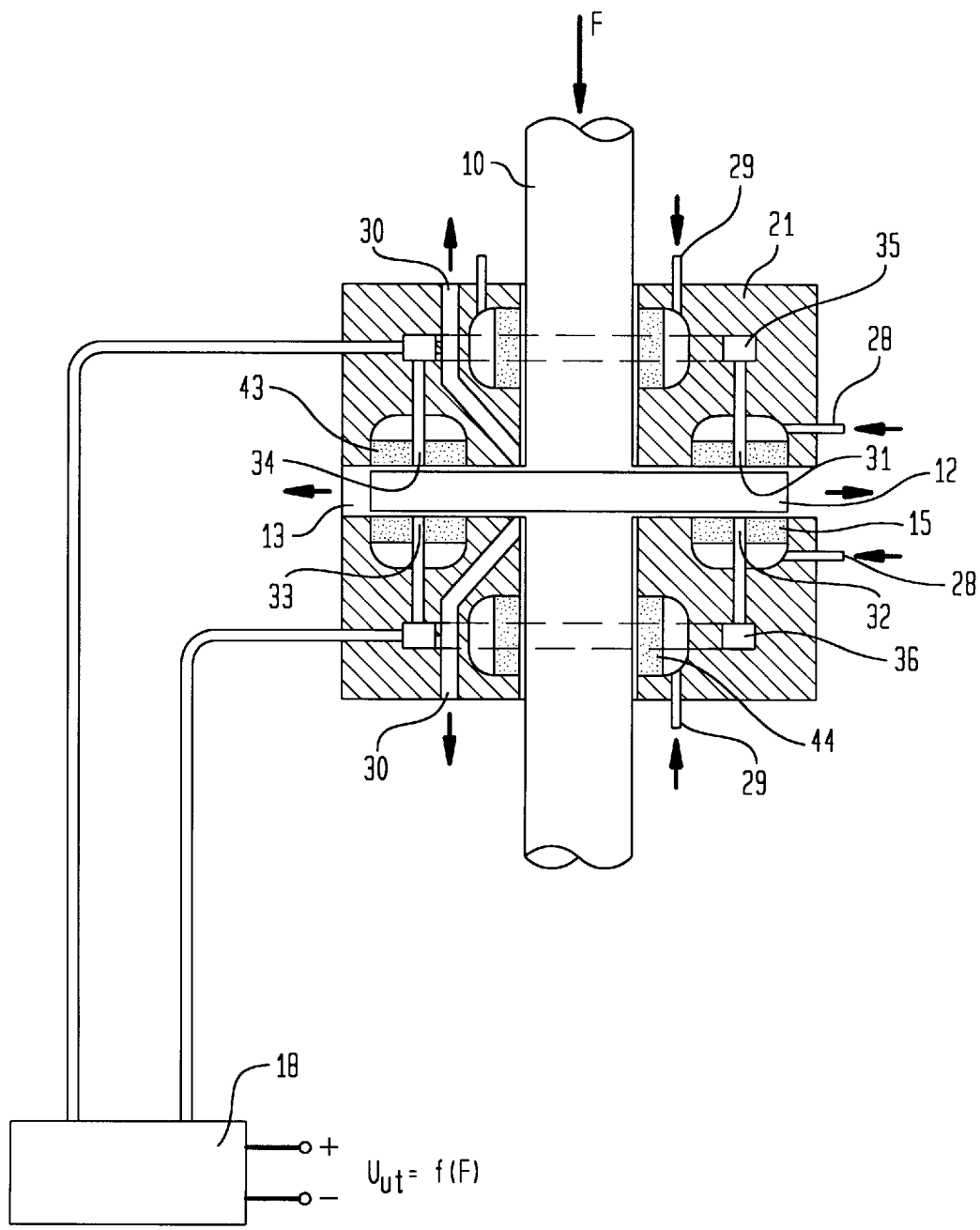
Figure 5:
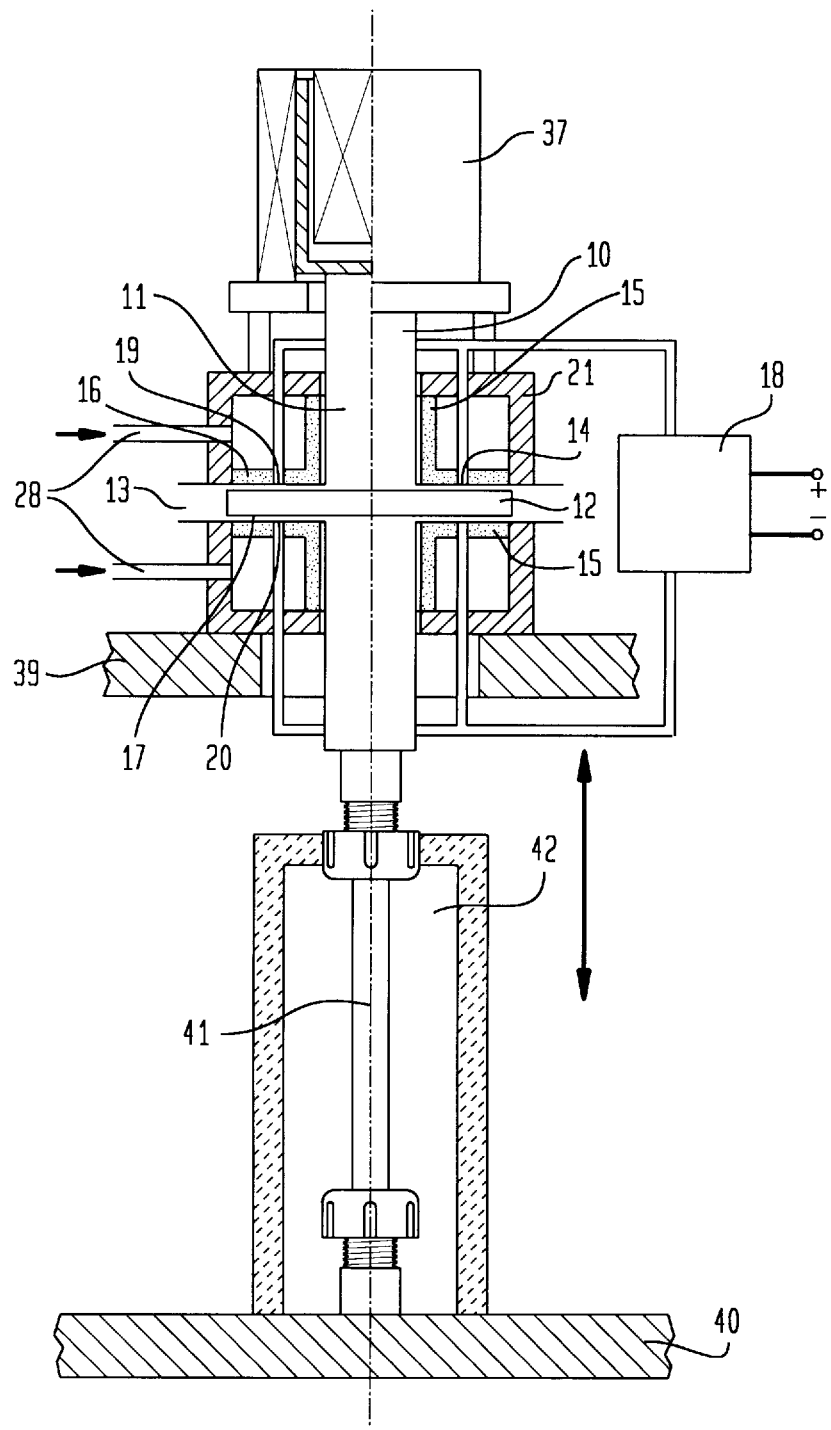
Figure 6:
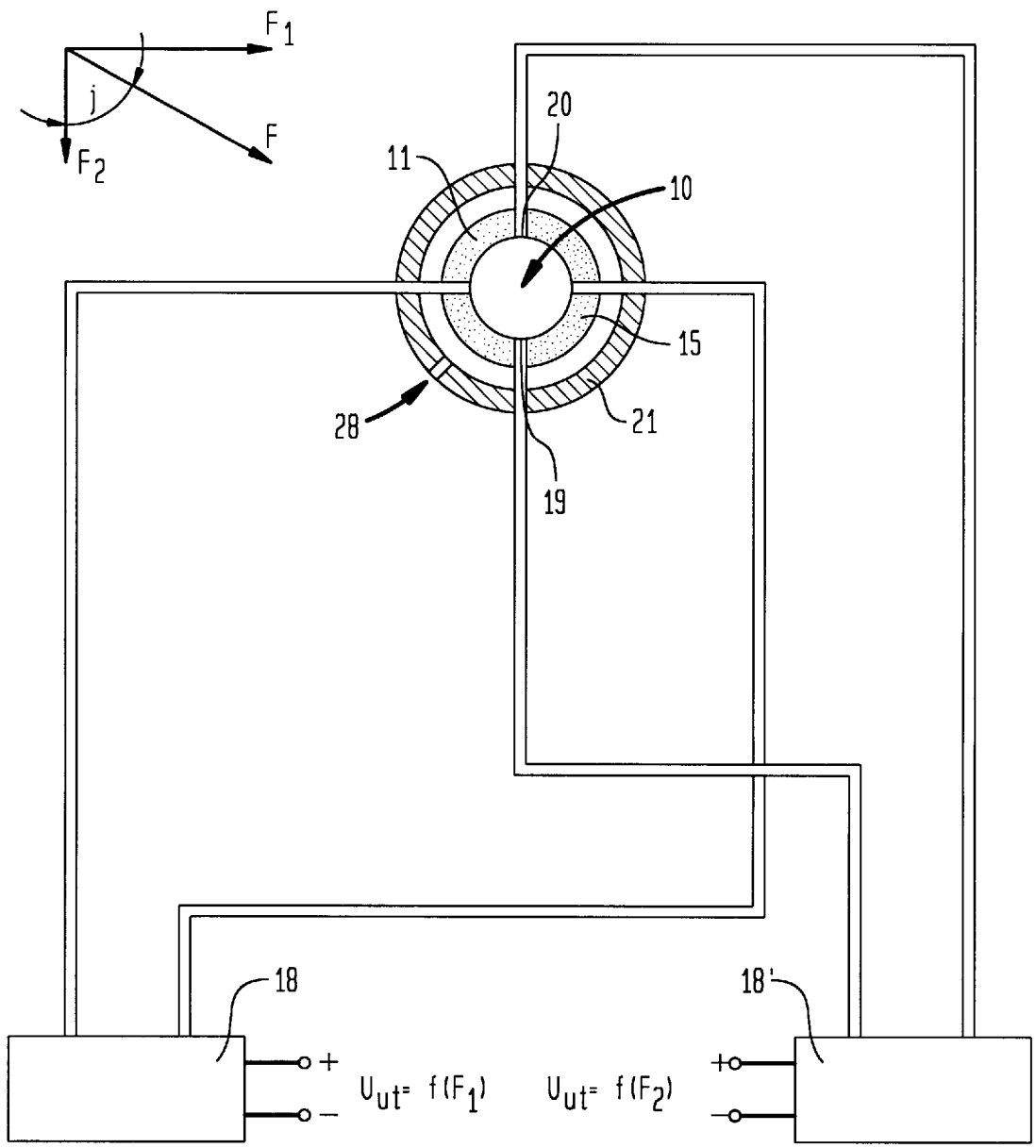
Figure 7:
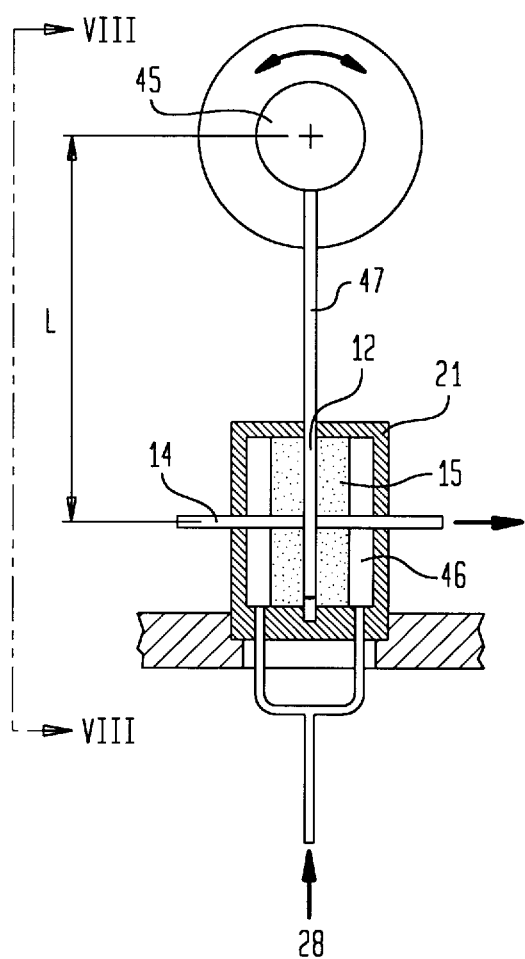
Figure 8:
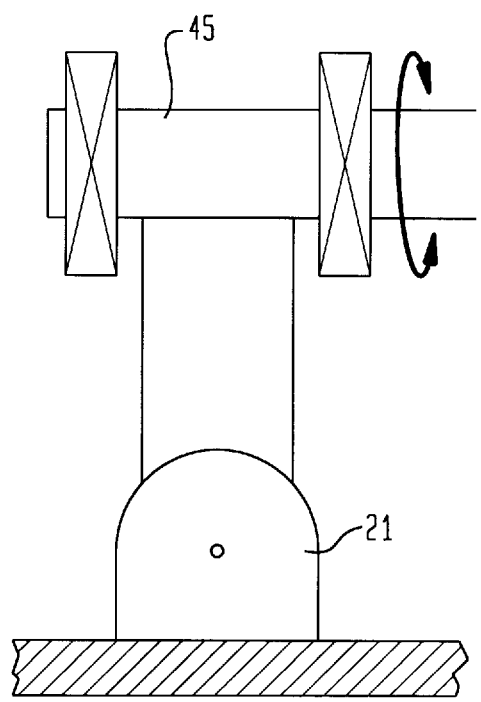

The invention will now be described in more detail with help of various examples of the invention with reference to the accompanying drawings of which FIG. 1 is a basic cross-sectional view of a device designed in accordance with the invention, FIG. 2 shows the device schematically according to FIG. 1 in conjunction with a Theological measuring assembly, FIG. 3 shows the device schematically according to FIG. 1 in conjunction with measuring bodies in a rheologically measuring assembly of a different embodiment than that described in FIG. 2, FIG. 4 shows an alternative embodiment with both axial air bearings and radial air bearings, FIG. 5 shows an alternative embodiment for measurement of various properties in rods, FIG. 6 shows an embodiment of a device in accordance with the invention for measuring radial loading and displacement, FIG. 7 is a sectional view of an alternative embodiment for measurement of torque, and FIG. 8 is a side view of VIII—VIII of the embodiment in FIG. 7.

DESCRIPTION

In the embodiment according to FIG. 1, a device in accordance with the invention holds a longitudinal shaft 10, which is borne rotating in an air bearing. The air bearing holds a body 15 which consists of two ring-shaped sections that surround portions of shaft 10, so that an air column 11 is formed between shaft 10 and body 15. Body 15 is permeable to air and is made suitably porous, for example, of graphite. Air column 11 functions also as the air bearing for shaft 10.

Between the two sections of body 15, a portion extends radially from shaft 10 in the form of a rotor with a rotor wheel 12. In the embodiment shown, rotor 12 is ring-shaped with two axially opposing sides, or faces, 16 and 17 and has essentially the same outer diameter as body 15. Gas under overpressure is conducted to body 15 in a conventional way via chambers. Body 15 with its two parts is surrounded by casing 21, through which channels 13 run as through holes or vents for air return.

A number of second channels running axially are provided in body 15 with outlets 19 and 20 axially directed towards both sides 16 and 17 of the radially projecting portion 12. Outlets 19 and 20 should be arrayed directly opposite each other for maximal precision in subsequent pressure measurements. In the embodiment shown the pressure measurement unit is in the form of a pressure differential sensor 18 connected with the outlets 19 and 20 for measuring the pressure difference between the pressures on the two sides 16 and 17 of the radially projecting portion 12. Differential pressure sensor 18 may be provided at an optional distance from outlets 19 and 20. Large volumes of gas in pressure lines between outlets 19 and 20 and the pressure differential sensor 18 can, however, complicate dynamic measurement.

When air, or another gas, is conducted to body 15 via channels 28, the air is distributed in body 15, streams through it, and exits via its pores or openings, so that a pressure film is built up which carries rotor 12 and even allows for a mechanical loading of it without the establishment of mechanical contact between the rotor and stator. The spacing, i.e. the air column or gap obtained between the rotor and stator, amounts in order of magnitude to 0.1 mm or less. When the rotor shaft is unloaded, wheel 12 assumes a position which gives the same pressure on both sides of the wheel. The agreement in pressure does not, however, necessarily mean that the air gap is of equal dimensions on both sides. The pressure force is, on the other hand, equal on both sides.

If shaft 10 is affected by an axial force, for example in the F direction of the arrow, the shaft and its radially projecting portion try to move in the direction of the arrow so that the air gap on the under side diminishes. When this occurs, the pressure between face 17 and the lower of the two sections of body 15 increases. The gap on the upper side increases as a result when the pressure falls. A difference thus occurs between the pressures outside the two ring-shaped faces of portion 12. The difference in pressure is directly related to the axial force. By determining the area of the two ring-shaped faces on portion 12 and measuring the pressure differences, the value of the force can be determined directly.

FIG. 2 shows schematically a practical design with the measuring assembly containing a conventional rheological measuring cell. The measuring device is identical to the one shown in FIG. 1. Shaft 10 is connected on the first end with a first measuring body 22 in the form of a circular plate. A second measuring body 23, which consists of a circular fixed plate, is connected with the first measuring body 22 via a test medium 24. The measuring device as per FIG. 2 is used for measurement of the viscoelastic properties of test medium 24. The shaft 10 is in a second end connected in a conventional way to a drive motor 37 for determining the viscoelastic properties of the test medium 24.

By including the measurement results of the pressure differential and axial force in the rheological measurement, a significantly more secure and comprehensive result is obtained. With this type of measurement it is also usual that test medium 24 is subjected to an exactly controlled increase of pressure. This is possible with a continual measurement of the axial force and controlled adjustment of the spacing between mounting planes 39 and 40.

In FIG. 3, a measuring device is shown which contains a rheological measurement cell of a more developed design. In this design, test medium 24 is contained in test chamber 25, which is delimited by the second measuring body 23 and column 11. By maintaining overpressure in column 11, pressurization of the test medium can be achieved.

The test medium is enclosed in a test chamber which is delimited by the outer, cylindrical measurement body 23 and a cover closing a measurement body with a column standing under overpressure and provided around shaft 10. Outer measurement body 23 is screwed into the cover and sealed with an O-ring.

The gap or column is provided in a first opening in the cover. Shaft 10 runs through a second opening displaced in relationship to the column in the axial direction of shaft 10 toward first measuring body 22. The difference between the outer diameter of shaft 10 and the inner diameter of the second opening is approximately 0.2 mm.

A space in the form of an antechamber 26 is located between the column and the second opening. Antechamber 26 is pressurized via the column and a third opening placed in the cover between antechamber 26 and the column. A fluid lock 27 surrounding shaft 11 is placed between test chamber 25 and antechamber 26.

Pressurization of the measuring cell is accomplished in the following manner. Gas, preferably air, is conducted to the sleeve or column under overpressure via pressure inlet 28. The air presses down through the third opening to antechamber 26. The pressure in the antechamber is somewhat lower than the pressure in pressure inlet 28. The pressure difference between antechamber 26 and atmospheric pressure can be great, and a part of the air will thus leak out into the atmosphere via the column. Since however the column has great air resistance, the leakage will be relatively insignificant.

Fluid lock 27, which in the embodiment shown contains a sleeve-shaped shoulder projecting vertically from the cover, has as a function of prventing test chamber ventilation. The pressure in the test chamber is equal to the pressure in the antechamber. In order to prevent the oxidation of sensitive samples, an inert gas can be injected directly into antechamber 26 using an overpressure. This can occur through a special opening in the antechamber or through a normally sealed drainage hole. The inert gas can also be conducted via an opening which is formed in the cover in order to make possible measurement of the pressure in the antechamber and thus also in the test chamber. A drive motor 37 drives shaft 10. Different parts of shaft 10 are connected with each other via a chuck 38.

As can be seen in FIG. 3, the measurement device is divided into an upper part with drive motor 37 and a lower part with the measuring bodies. The upper part is fixed in a first mounting plane 39, and the lower part in a second mounting plane 40. The spacing between the mounting planes is adjustable.

In the alternative embodiment in FIG. 4, there are provided separate axial air bearings 43 and radial air bearings 44. Gas under overpressure is conducted to the axial air bearings 43 via first channels 28 and to the radial air bearings 44 via second channels 29. Return or superfluous gas exhausts partly from channels 13 and 30 and partly as leakage around shaft 10. Gas vents 31, 32, 33, and 34 are present in axial air bearings 26 opposite each other on both sides of wheel 12. Preferably said gas vents are present in pairs opposing each other radially and at the half radius out from the center line of shaft 10. The gas vents should thus be positioned where the pressure is highest. All of the gas vents 31, 32, 33, and 34 open into equalization chambers 35 and 36 in which a mean pressure value is maintained in the column between wheel 12 and the bearings. In this way the measurement is less dependent on other interfering loads, for example, forces which exert themselves perpendicularly against shaft 10. The pressure differential is then measured between the two equalization chambers with a pressure differential sensor whose output reading is proportional to the force and whose polarity indicates the direction (pull or push force). Since a given axial force on the shaft must be balanced by a corresponding pressure differential in the axial bearing, the sensor remains independent of moderate variations in the pressure into the air bearing.

It is also possible to achieve the opposite effect. If the air pressure into the air bearing is held constant, the sensor can be used to measure the axial displacement of the rotor in the stator. Calibration is necessary for this kind of measurement.

In all embodiments of the measuring device according to the invention the measurement of pressure can be carried out in alternative ways. It is, for example, possible to set up pressure sensors in body 15 or in direct connection with portion 12. The pressures on both sides of portion 12 can also be measured individually when a value of the pressure differential between the sides is determined with a means of calculation or control device, for example, a processor.

The embodiment as per FIG. 5 is intended for uses in measuring various characteristics of rods, above all their elastic properties. A rod 41 is connected with shaft 10 and is provided internally in chamber 42, which functions as an oven. The oven is heated in a controlled manner to the desired temperature by a heating device not shown. The various properties of rod 41 are measured at different temperatures.

When the temperature in the oven increases, rod 41 expands and axial forces arise in shaft 10. These axial forces affect the measurement. With certain types of measurements attention must be paid to the axial forces, but in other applications the forces are undesirable. The forces can also become so great that the air bearing can be damaged. By continuously measuring the occurring axial forces it is possible both to include them in the measurement and to avoid the occurrence and effect of them. Avoidance can be achieved by letting the output from pressure sensor 18 control the longitudinal displacement tool changing the distance between mounting plates 39 and 40.

In the embodiment as per FIG. 6, body 15 is equipped with channels directed radially toward the shaft with openings 19 and 20 on the corresponding sides of shaft 10. Two more channels with openings are set at a right angle toward the before-mentioned openings 19 and 20. The force diagram sketched in FIG. 6 illustrates that a radial force which acts on shaft 10 will cause pressure differences on each side of the shaft in a way corresponding to what was described above. A first pressure differential is obtained as a result of a force which works in line with a first radius, and a second pressure differential is obtained as a result of a force which works in line with a second radius perpendicular to the first radius. The measured pressure differentials correspond to two perpendicularly working force components $F_1$ and $F_2$, the resultant of which corresponds to the actual force F.

Just as in the embodiments described above, an embodiment as per FIG. 6 can be used for determination of shaft displacement, in this case in the radial direction instead of in the axial direction, as an alternative to determination of the impinging force.

In the embodiment as per FIG. 7, measuring plate 12 is inserted in a slit in body 15, which consists of two parallel disks. The disks are enclosed in a casing 21. Gas under overpressure is conducted in the way described above into chamber 46 from air induction channels 28. The gas intrudes through the two disks in body 15 and forms a gas layer between body 15 and measuring plate 12.

Measuring plate 12 includes an elongated part 47 which protrudes from casing 21 and is connected rigidly with measuring shaft 45. In the embodiment shown elongated part 47 is provided so as to be directed radially toward shaft 45. Other angles between shaft 45 and measuring plate 12 can also be set. When shaft 45, which is also shown in FIG. 8, is subjected to a torque, the corresponding force is transmitted to measuring plate 12. This force is balanced in the way described above, and the pressure differential arising between the two sides of measuring plate 12 constitutes a measurement of the force exerted on the measuring plate 12. According to the above, the pressure differential is measured through channels 14 in body 15, which open centrally toward measuring plate 12. A lever L between the center line of shaft 45 and a middle point on measure plate 12 is used to determine the torque which affects shaft 45.

In another embodiment not shown, elongated part 47 is pivotably connected with a support device fixed in relationship to body 15. Forces which affect elongated part 47 in other directions than in its longitudinal direction cause a force directed along a normal on the measuring plate. This force in the direction of the normal is determined in the same way as was described above.

In the two measuring devices described directly above, the balancing function in the measuring assembly entails very small deviations of angle in elongated part 47, for which reason possible mistakes in measuring will also be small or insignificant. The balancing function in the measuring device according to the invention also entails generally that problems with drift in amplifiers and other electrical components in pressure differential sensors 18 and control apparatuses connected to them can be minimized or completely eliminated.

If the pressure is measured on only one side, corrections will additionally be required with respect to the basic pressure present in the air bearing on an unloaded shaft, among other things. The absolute pressure which in such a case is measured on one of sides 16 and 17 must be put in relationship to the basic pressure. The varying pressure difference which occurs between measured pressure and the basic pressure constitutes in this case the measuring output, which is used to determine the force on the shaft. The pressure difference is not linear in relation to the force on the shaft but rather follows a more complicated function, for which reason further corrections or calculations are required.

It is also possible to use gas pressure on only one side. In such a case a necessary counter force must be applied on the other side, for example with a magnet. The air bearings used in various applications and body 15 can also be equipped with the so-called "jet type," i.e., they are furnished with a number of holes through which gas is conducted under overpressure. The inflow occurs then in discrete points.

I claim:

1. A method for measurement of forces acting axially on a shaft, said shaft having a portion protruding from said shaft, said portion having a first and second opposing side, comprising the steps of:

supplying gas under overpressure; and providing at least one gas-permeable body outside of at least one of said opposing sides, wherein a gas pressure is built up between at least one of said opposing sides of said portion protruding from the shaft and a gas pressure on at least one of said opposing sides is measured and that the force acting axially on the shaft is determined as a function of the measured gas pressure.

2. The method according to claim 1, wherein a pressure differential is measured between the gas pressures on said opposing sides and that the force acting axially on said shaft is determined as $k*\Delta P$, with k being a constant and $\Delta P$ being the pressure differential between the gas pressures on said opposing sides.

3. A measuring device comprising:

a rotative shaft for measurement of axial forces acting on a shaft, at least one gas-permeable body positioned on the outside of said shaft with a column standing under pressure between the outer envelope surface of the shaft and said body;

a protruding portion protruding from said shaft extending through said body with play, said protruding portion having two axially opposing sides;

means for supplying gas under overpressure to said body; and pressure measuring means for measurement of pressure on at least one of said two sides of said protruding portion, wherein the force acting on said shaft is a function of the measured pressure.

4. The measuring device according to claim 3 further comprising:
   a plurality of second channels extending axially in said body, each of said channels having an outlet directed axially toward said two opposing sides of said protruding portion and said second channels are connected to said pressure measuring means.

5. The measuring device according to claim 4, wherein said body is surrounded by a sealed casing.

6. The measuring device according to claim 5, wherein said body comprises at least one porous, gas-permeable sleeve.

7. The measuring device according to claim 5, wherein said shaft has a first end connected to a first measuring body with a test medium for measurement of the viscoelastic properties of said test medium.

8. The measuring device according to claim 7, wherein said test medium is enclosed in a test chamber, which is defined by said second measuring body and said column, the over pressure of said column causing the test medium to be put under pressure.

9. The measuring device according to claim 5, wherein said body is connected to a first mounting plate, said shaft is connected to a second mounting plate and said first mounting plate and said second mounting plate are movable relative to each other in the axial direction of said shaft.

10. A method for measurement of radial forces acting on a shaft comprising the steps of:
   supplying the outer envelope surface of said shaft with gas under overpressure, gas pressure is built up in a space between the envelope surface and at least one gas-permeable body adjacent to the envelope surface;
   measuring a first pressure differential between said gas pressure on two radially opposing first portions of said space; and
   measuring a second pressure differential between gas pressure on two radially opposing second portions of said space, said first and second portions being provided perpendicularly to each other,
   wherein the resulting pressure differential is determined as the difference between said first and second pressure differentials, and the radial force acting on said shaft is determined as k*ΔP, with k being a constant and ΔP being the resulting pressure differential.

11. A method for measurement of forces comprising the steps of:
   supplying at least one of two opposing faces of a measuring plate with gas under overpressure such that gas pressure is built up between at least one of said two opposing faces and at least one gas-permeable body provided external to said opposing faces; and
   measuring gas pressure on at least one of said opposing faces,
   wherein the force acting on one of said faces is determined as a function of the measured gas pressure.

12. The method for measurement of forces according to claim 11, wherein said two opposing faces of a measuring plate are supplied with gas under overpressure in such a way that gas pressure is built up between said two opposing faces and at least one gas-permeable body external to said opposing faces, gas pressure between the gas pressures on said opposing faces is established and the force acting on one of said faces is determined as k*ΔP, with k being a constant and ΔP being the pressure differential between the gas pressures on said two opposing faces.

13. The method according to claim 12, wherein said gas is supplied through the gas-permeable body.

14. The method according to claim 12, wherein said gas is supplied to the gas-permeable body through open chambers.

15. A measuring device for measurement of forces on a measuring plate comprising;
   said measuring plate provided with at least one body having at least one of two opposing faces of said measuring plate turned toward gas-permeable surfaces of the body;
   means for supplying gas under overpressure to said body; and
   pressure measuring means for measurement of gas pressure on at least one of the two faces of the measuring plate,
   wherein the force acting on the measuring plate is a function of the measured gas pressure.

16. The measuring device according to claim 15, wherein said measuring plate is provided in said turned toward gas-permeable surfaces of the body, said pressure measuring means are provided for measurement of the pressure differential between the pressures on said two faces of the measuring plate, the pressure differential constituting a measure for the force acting on the measuring plate.

17. The measuring device according to claim 16, wherein said measuring plate is rigidly connected to and protruding from a shaft, said shaft being subjected to a torque.

18. The measuring device according to claim 16, wherein said measuring plate protrudes in the radial direction of said shaft.

19. The measuring device according to claim 16, wherein a portion of said measuring plate protruding from said body is articulated connected with a support device fixed relative to said body.

* * * * *